(12) United States Patent
Risto et al.

(10) Patent No.: US 8,287,565 B2
(45) Date of Patent: Oct. 16, 2012

(54) RETRACTOR

(75) Inventors: Olof Risto, Linköping (SE); Stefan Lind, Jönköping (SE)

(73) Assignee: Surg-Mate AB (SE)

( * ) Notice: Subject to any disclaimer, the term of this patent is extended or adjusted under 35 U.S.C. 154(b) by 506 days.

(21) Appl. No.: 11/722,879

(22) PCT Filed: Dec. 27, 2005

(86) PCT No.: PCT/SE2005/002043
§ 371 (c)(1),
(2), (4) Date: Jun. 26, 2007

(87) PCT Pub. No.: WO2006/071188
PCT Pub. Date: Jul. 6, 2006

(65) Prior Publication Data
US 2008/0021286 A1    Jan. 24, 2008

(30) Foreign Application Priority Data
Dec. 29, 2004   (SE) ...................................... 0403211

(51) Int. Cl.
*A61B 1/32* (2006.01)
(52) U.S. Cl. ....................................................... 606/206
(58) Field of Classification Search .................. 600/191, 600/206, 212, 185–190, 192–205, 207–211, 600/213–249
See application file for complete search history.

(56) References Cited

U.S. PATENT DOCUMENTS

| | | | | |
|---|---|---|---|---|
| 1,450,419 A * | 4/1923 | Heidbrink | ...................... | 600/237 |
| 1,727,879 A * | 9/1929 | Hodlick et al. | ................ | 600/219 |
| 2,238,563 A * | 4/1941 | Jacques | .......................... | 27/21.1 |
| 2,651,300 A * | 9/1953 | Fehrman | ......................... | 600/244 |
| 3,766,910 A | 10/1973 | Lake | ................................ | 128/20 |
| 3,774,438 A * | 11/1973 | Weston | ........................ | 72/409.01 |
| 3,841,318 A * | 10/1974 | Olson | ............................ | 600/220 |
| 3,916,880 A * | 11/1975 | Schroer | .......................... | 600/205 |
| 4,442,837 A * | 4/1984 | Keatley | .......................... | 606/131 |
| 4,541,428 A * | 9/1985 | Scherrer | ........................ | 606/174 |
| 4,834,096 A * | 5/1989 | Oh et al. | ......................... | 606/158 |
| 4,953,266 A * | 9/1990 | Trinkaus | ......................... | 24/499 |
| 5,002,323 A * | 3/1991 | Idsund | ........................... | 294/100 |

(Continued)

FOREIGN PATENT DOCUMENTS
CA   2 277 749   1/2000
(Continued)

OTHER PUBLICATIONS

Swedish Official Action dated Mar. 10, 2011, Appln. No. 1000868-8 (6 pgs).

(Continued)

*Primary Examiner* — Alvin Stewart
*Assistant Examiner* — Jerry Cumberledge
(74) *Attorney, Agent, or Firm* — Hayes Soloway P.C.

(57) ABSTRACT

A retractor (1) that is meant to be placed in a wound (7) to hold this open during a surgical operation, comprising a shackle of a plastic material pervious for X-ray radiation. The shackle has to resilient legs (2a, 2b), that in a resilient way can be brought towards each other from a starting position in order to be inserted into the wound (7) and thereafter through resilient return towards the starting position be brought to contact with the edges of the wound (7) and thereby holding these apart and in a self-holding way fasten the retractor (1) in the wound (7).

10 Claims, 3 Drawing Sheets

U.S. PATENT DOCUMENTS

| | | | |
|---|---|---|---|
| 5,019,091 A * | 5/1991 | Porat et al. | 606/205 |
| 5,070,860 A | 12/1991 | Grounauer | |
| 5,163,419 A | 11/1992 | Goldman | 128/20 |
| 5,176,129 A | 1/1993 | Smith | 128/20 |
| 5,433,190 A * | 7/1995 | Sunalp | 600/236 |
| 5,441,040 A * | 8/1995 | Williams, Jr. | 600/236 |
| 5,487,746 A * | 1/1996 | Yu et al. | 606/151 |
| 5,499,431 A * | 3/1996 | Mortensen et al. | 24/543 |
| 5,620,452 A | 4/1997 | Yoon | 606/151 |
| 5,683,405 A * | 11/1997 | Yacoubian et al. | 606/158 |
| 5,766,189 A * | 6/1998 | Matsuno | 606/158 |
| 5,906,642 A * | 5/1999 | Caudillo et al. | 606/1 |
| 6,136,017 A | 10/2000 | Craver et al. | 606/205 |
| 6,276,644 B1 * | 8/2001 | Jennings et al. | 248/49 |
| 6,440,065 B1 * | 8/2002 | Hered | 600/236 |
| 6,544,169 B2 * | 4/2003 | Putrino et al. | 600/236 |
| 6,662,598 B2 * | 12/2003 | Meehan | 63/12 |
| 6,702,739 B2 * | 3/2004 | Levisman | 600/217 |
| 7,520,882 B2 * | 4/2009 | Muramatsu et al. | 606/142 |
| 2002/0087051 A1 | 7/2002 | Levisman | 600/209 |
| 2002/0103421 A1 | 8/2002 | Putrino et al. | 600/236 |
| 2005/0033324 A1 * | 2/2005 | Phan | 606/148 |

FOREIGN PATENT DOCUMENTS

| | | |
|---|---|---|
| CA | 2 443 265 | 10/2002 |
| DE | 90 16 499.7 | 4/1991 |
| DE | 100 01 695 | 2/2001 |
| GB | 287529 | 12/1928 |
| GB | 1 520 832 | 8/1978 |
| JP | 6-75417 | 10/1994 |
| JP | 11-137558 | 5/1999 |
| JP | 2000-60861 | 2/2000 |
| JP | 2001-516261 | 9/2001 |
| JP | 2004-216494 | 8/2004 |
| JP | 2004-525716 | 8/2004 |
| WO | WO 2006/071188 | 7/2006 |

OTHER PUBLICATIONS

European Supplementary Search Report dated Dec. 27, 2010, Appln. No. 05819823.5-2310/1833377 (PCT/SE2005002043) (6 pgs).
Japanese Official Action and translation dated Jul. 12, 2011.
Examiner's Report for corresponding Canadian application No. 2,612,652, dated Apr. 5, 2012 (3 pgs).

* cited by examiner

RETRACTOR

TECHNICAL AREA

This invention concerns a retractor, which is intended to be placed in a wound in order to hold this open during a surgical operation.

TECHNICAL BACKGROUND

A known retractor of this kind comprises a curved hook of metal that is inserted into a wound and pulled laterally against a wound edge in order to hold the wound open and in that way facilitate a surgical operation. Advantageously two retractors are used, which are pulled in opposite directions in order to hold the wound as open as possible. A drawback with such a retractor is that it requires a person holding it during the entire operation. Another drawback is that the retractor at an X-ray examination may block out for instance a fractured bone that is to be X-rayed, which involves the removal of the retractor during the examination. A further drawback is that the retractor after use must be subjected to an extensive cleaning when it is washed, sterilized and repacked before it can be used at a new surgical operation.

SUMMARY OF THE INVENTION

The object of the invention is therefor to provide a retractor, that is so constructed that the above problems are eliminated. This object is in accordance with the invention achieved with a retractor of the above mentioned kind and is characterized in that it is constituted of a shackle of a plastic material that is pervious for X-rays, which has two resilient legs that in a springy way can be brought together from a starting position in order to be inserted into the wound or cut and thereafter through resilient return towards the starting position be brought to contact with the edges of the wound and thereby holding these apart and in a selfsupporting way fasten the retractor in the wound.

Since the retractor is made of a plastic material pervious for X-rays it can remain in the wound during X-ray examination without blocking for instance a bone fracture that is to be X-rayed.

The retractor is made of plastic material and intended to be used as a one-time product, which makes it hygienic and which means that no extensive and costly cleaning work must be carried out.

The two resilient legs of the retractor are pressed out against the edges of the wound when the retractor is placed in the wound and makes the retractor self holding, resulting in that one need not to hold the retractor during the surgical operation once it has been placed in the wound.

Since each leg in its free end has an outwards directed, hook-like protrusion for gripping a wound edge the retractor is better located in the wound.

The legs of the retractor have preferably each a knee like bend, the bends being located opposite each other. This means that a larger space is obtained above the wound, which facilitates the surgical operation.

The shackle of the retractor is preferably made in one peace which simplifies the fabrication process. Advantageously for X-ray radiation pervious material in accordance with the invention may be used for retractors in a wide meaning, that is means that at surgical operations are used to hold apart tissues and parts of the body. For example the type of retractors that are used to hold muscle and sinew tissues at a distance from bones that are to be worked, and then in particular on the bottom side. Since it becomes possible to X-ray with the retractors in place one can better and more easily than before secure that the bone on the off side is free so that the muscles do not risk to be injured at the working of the bone.

SHORT DESCRIPTION OF THE DRAWINGS

Below the invention will be described in more detail with reference to the enclosed drawings.

DESCRIPTION OF A PREFERRED EMBODIMENT

Figure 1:
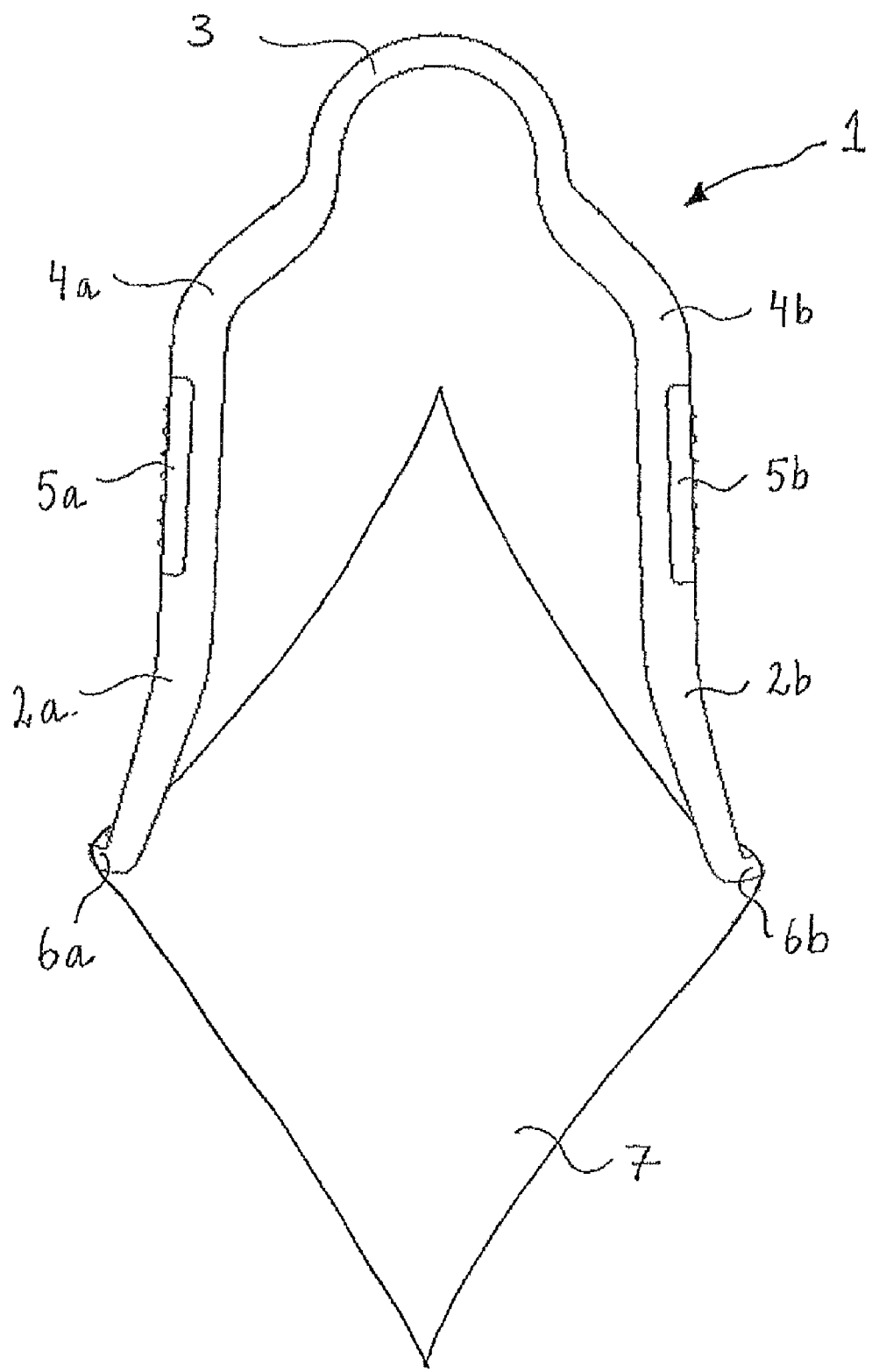
FIG. 1 is a frontal view showing a retractor according to the invention in a starting position.

In the drawings a retractor 1 in accordance with the invention is shown. The retractor 1 is constituted of a shackle that has two elongate, resilient legs 2a, 2b and an essentially part circular spring head 3, from which the legs 2a, 2b extend. The retractor 1 is made in one piece and of a plastic material pervious for X-ray radiation, preferably environment friendly decomposable hard plastic.

Figure 2:
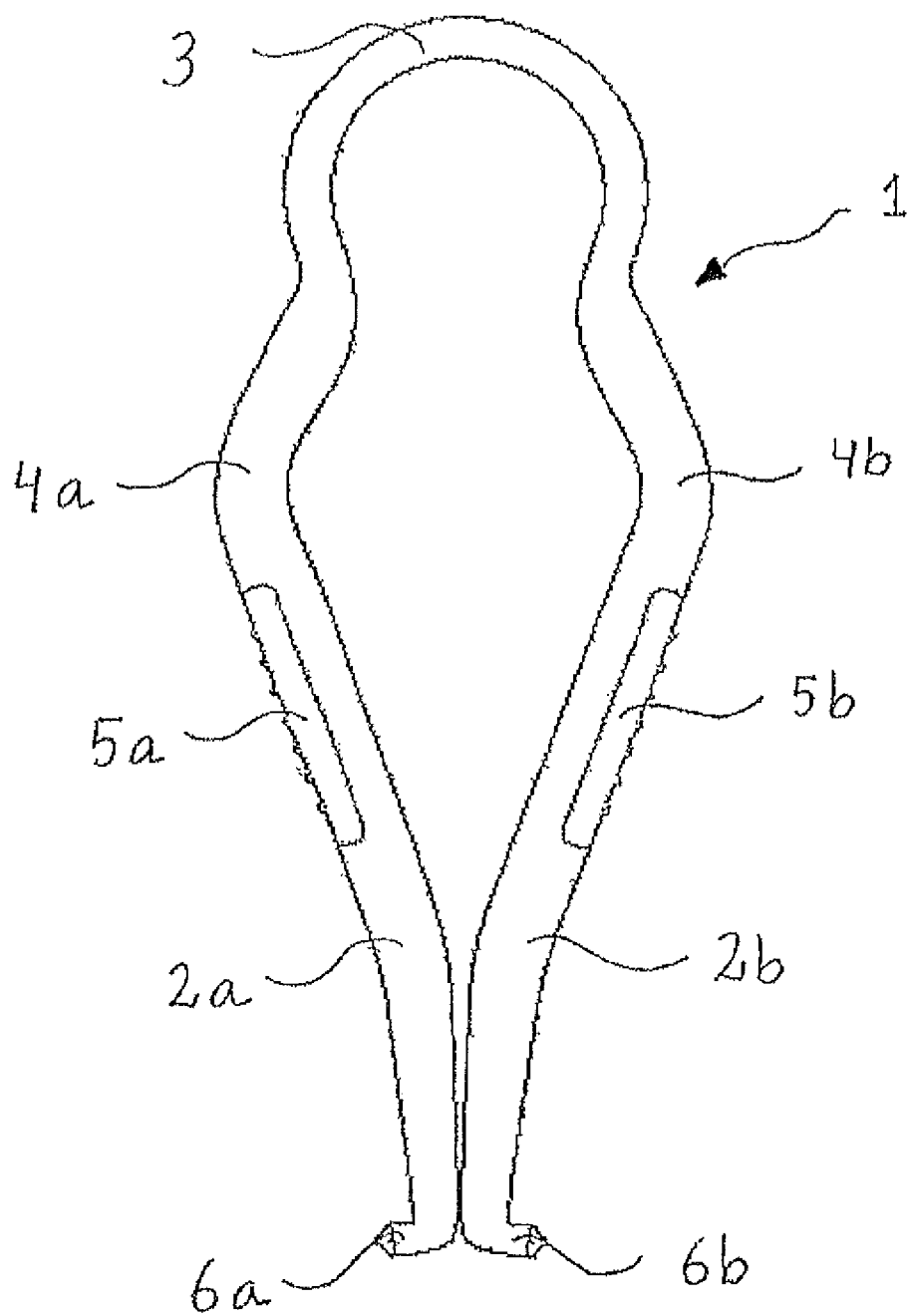
FIG. 2 is a frontal view showing the retractor of FIG. 1 in a compressed position.

The two legs 2a, 2b are in a resilient way possible to bring together from a starting position (FIG. 1), in which there is a distance between the lower parts of the legs 2a, 2b, to an entirely compressed position (FIG. 2), in which the legs 2a, 2b are in contact with each other in their lower parts.

The legs 2a, 2b have each a knee like bend 4a, 4b. The bends 4a, 4b are located opposite each other. In the proximity of each bend 4a, 4b a grip 5a, 5b is arranged. The grips 5a, 5b have an uneven surface structure.

Each leg 2a and 2b have furthermore in their free ends an outwards directed hook-like protrusion 6a, 6b that is a short extension of each leg 2a, 2b.

The retractor 1 is at use inserted into a wound 7, in order to hold this open during a surgical operation.

When the retractor 1 is to be inserted into the wound 7 the legs 2a and 2b are pressed together (FIG. 2) by the user pushing the grips 5a, 5b towards each other so that the lower parts of the legs 2a, 2b are brought in contact with each other. Thereafter the retractor 1 is inserted into wound 7. When the user releases the pressure on the grips 5a, 5b the legs 2a, 2b are once again separated and contact the edges of the wound 7. The resilient return of the legs 2a, 2b towards the starting position result in the edges of the wound 7 being held apart. The inherent resilience of the retractor 1 causes the retractor 1 to be seated on location in the wound 7 in self supporting manner.

The grips 5a, 5b facilitate the pressing together of the legs 2a, 2b, since they help the user to get a steady grip on the retractor 1. The grips 5a, 5b also reduce the risk for the user to slip and injure the edges of the wound 7.

The outwards directed, hook-like protrusions 6a, 6b are brought to contact with the edges of the wound 7 when the retractor is placed in the wound 7 and result in a safe seating of the retractor in the wound 7.

Below the resilient head 3 of the retractor 1 and between the bends 4a, 4b a space is formed that provides space for the hands of the user and possible instruments that are used during the surgical operation which facilitates the executing of the surgical operation.

Within the frame of the inventive thought one can also consider other embodiments of the retractor than the one described above, for instance the legs of the retractor may be straight instead of being bent outwards in the ends. One can further consider the legs being bent more or less downwards a distance from the hooks or tips, depending on what they are intended to be used for. Either with the legs straight or as in FIG. 1 bent slightly outwards. At this also the tips may be considerably longer.

Figure 3:
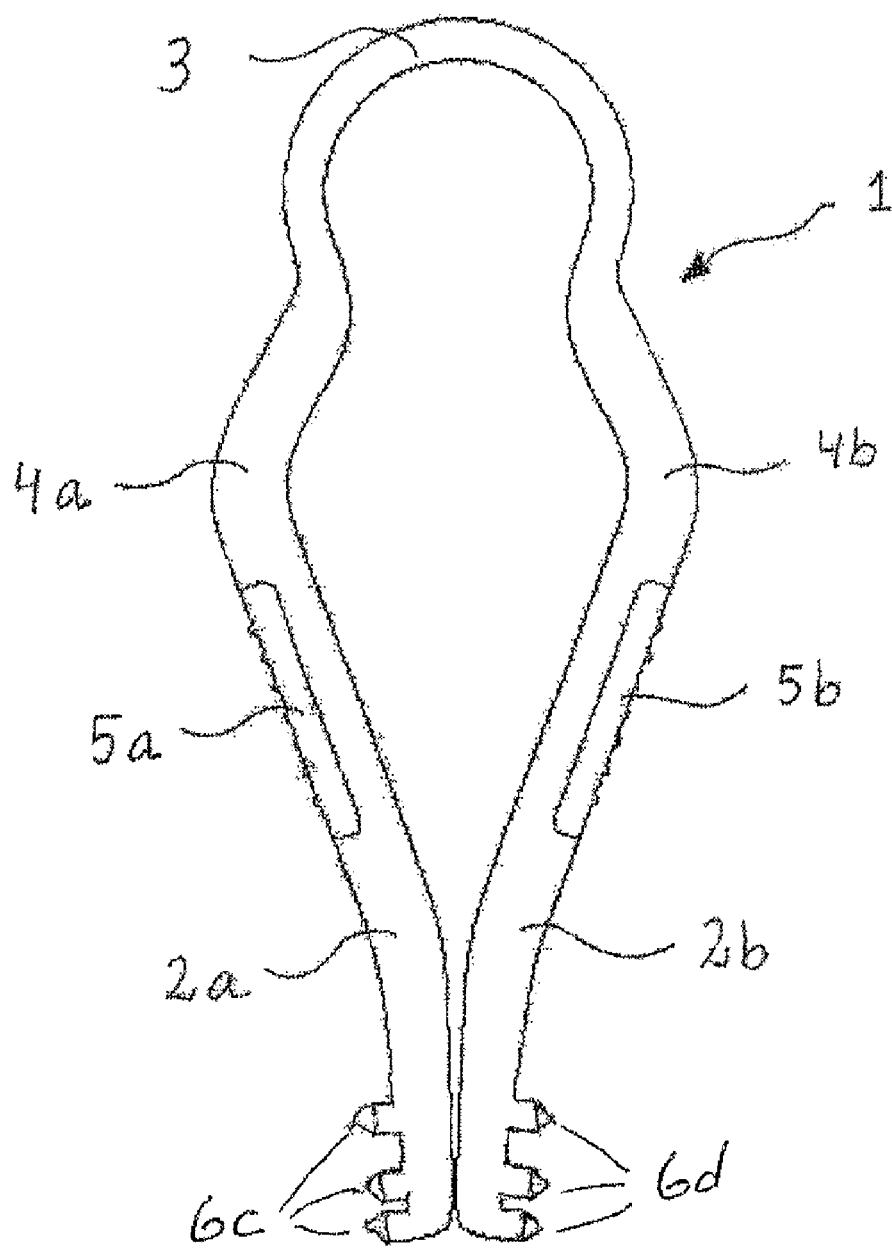
FIG. 3 is a view similar to FIG. 2 showing an alternative embodiment of a retractor according to the invention.

Referring now to FIG. 3, in order to achieve a more gentle and a possibly more elongate separating of the wound edges the retractor in accordance the with invention may instead of the two hooks be provided with a number of parallel downwards extending hooks 6c, 6d, approximately as a comb or fence, but where each tooth in the lower end ends with one or several outwards directed points. The force is at this distributed to several points and since the wound edges can be held apart over a greater length the separation in the middle need not to be as large for the same operation with. Furthermore one can by using retractors of this type do with less retractors, which may improve the accessibility to the operation area. If so desired each comb tooth or hook may be slightly resilient in order to secure an even force distribution. The points in the end of the retractor may also have different length depending on the field of application.

Furthermore the retractor in accordance with the invention may at the location for the gripping at compressing be provided with grip parts extending above the plane of retractor and that may be grooved and/or concave to reduce the risk that one at gripping slip or need to use unnecessarily much time to get a god grip.

A suitable material for the retractor in accordance to the invention is polyamide or polyoxymethylene that easily can be destructed through burning.

The invention claimed is:

1. A retractor for placement in a wound to hold the wound open during a surgical procedure comprising a shackle formed of a plastic material permeable to X-ray radiation, said shackle having two legs having proximal and distal ends, wherein the legs are joined at their proximal ends at a substantially semi-circular spring head such that the distal ends can be brought together from a starting position to enable insertion of the retractor into the wound and thereafter through resilience return towards the starting position and brought in contact with edges of the wound and hold the wound edges apart and in a self-holding way fasten the retractor in the wound, and wherein the legs each have a first bend, outward from an axis running lengthwise through the center of said retractor, and a second bend inward towards said axis, said second bend at a position distal to said first bend such that the length of the portions of the legs distal to the second bend is substantially greater than the length of the portions of the legs proximal to the second bend, said first and second bends being configured such that the portions of the legs distal to the second bends extend substantially in the same direction as the ends of the semi-circular spring head proximal to the first bend of the legs, and the space between the legs at a position distal to the second bend is substantially greater than the space between the legs at a position proximal to the second bend when the retractor is in the starting position.

2. The retractor of claim 1, wherein each leg at its distal end has a hook-like protrusion directed outwards from an axis running lengthwise through the center of said retractor for gripping of a wound edge.

3. The retractor of claim 1, wherein the bend is a knee like bend, wherein the bends are located opposite each other.

4. The retractor of claim 1, wherein the shackle is made in one piece.

5. The retractor of claim 1, wherein the legs are bent downwards a distance from their distal ends.

6. The retractor of claim 1, wherein the legs of the retractor at their distal ends are provided with a row of downward extending thin pins that in the lower ends are provided with one or several outward facing points.

7. The retractor of claim 1, wherein the legs are provided with upwards protruding grip parts.

8. The retractor of claim 1, wherein the plastic material comprises a decomposable hard plastic material.

9. The retractor of claim 1, wherein the plastic material comprises polyoxymethylene.

10. The retractor of claim 1, wherein the grips have uneven surfaces.

* * * * *